United States Patent
Williamsson et al.

Patent Number: 5,674,457
Date of Patent: Oct. 7, 1997

[54] CAPILLARY MICROCUVETTE

[75] Inventors: Anders Williamsson, Helsingborg; Stefan Wahlqvist, Lomma; Sven-Erik Nilsson; Jan Lilja, both of Helsingborg; Lars Jansson, Ängelholm; Bertil Nilsson, Bjärred, all of Sweden

[73] Assignee: Hemocue AB, Ängelholm, Sweden

[21] Appl. No.: 429,494

[22] Filed: Apr. 26, 1995

[51] Int. Cl.$^6$ ................................................ B01L 3/00
[52] U.S. Cl. ........................ 422/102; 422/104; 422/99; 356/246
[58] Field of Search ........................ 422/99, 100, 102, 422/104; 356/246, 440

[56] References Cited

U.S. PATENT DOCUMENTS

| | | | |
|---|---|---|---|
| 2,015,949 | 10/1935 | Maw | 356/246 |
| 2,056,791 | 10/1936 | Logan | 356/246 |
| 2,059,374 | 11/1936 | Logan et al. | 356/246 |
| 2,062,587 | 12/1936 | Logan et al. | 356/246 |
| 2,062,588 | 12/1936 | Logan et al. | 356/70 |
| 2,069,374 | 2/1937 | Lagomarsino | 62/298 |
| 3,363,503 | 1/1968 | Shifrin | 356/246 |
| 3,501,242 | 3/1970 | De Mey, II et al. | 356/246 |
| 3,565,537 | 2/1971 | Fielding | 356/246 |
| 3,698,822 | 10/1972 | Polanyi | 356/246 |
| 3,705,000 | 12/1972 | Guerra | 356/246 |
| 3,814,522 | 6/1974 | Clark et al. | 356/197 |
| 4,088,448 | 5/1978 | Lilja et al. | 422/102 |
| 4,088,488 | 5/1978 | Chang et al. | 96/29 D |
| 4,405,235 | 9/1983 | Rossiter | 356/246 |
| 4,596,695 | 6/1986 | Cottingham | 422/58 |
| 4,746,215 | 5/1988 | Gross | 356/339 |
| 4,756,884 | 7/1988 | Hillman et al. | 422/73 |
| 4,761,381 | 8/1988 | Blatt et al. | 436/165 |
| 4,865,812 | 9/1989 | Kuntz et al. | 422/99 |
| 4,957,582 | 9/1990 | Columbus | 156/332 |
| 4,981,654 | 1/1991 | Kuntz et al. | 422/102 |
| 5,030,421 | 7/1991 | Muller | 422/102 |
| 5,147,607 | 9/1992 | Mochida | 422/57 |
| 5,260,032 | 11/1993 | Muller | 422/102 |

FOREIGN PATENT DOCUMENTS

| | | |
|---|---|---|
| 0 287 883 | 10/1988 | European Pat. Off. |
| 2-17426 | 1/1990 | Japan |

OTHER PUBLICATIONS

"An Azide-Methemoglobin Method for Hemoglobin Determination in Blood", Guilio Vanzetti, J. Lab. & Clin. Med., vol. 67, No. 1, pp. 116-126, Jan. 1966.

*Primary Examiner*—Harold Pyon
*Attorney, Agent, or Firm*—Burns, Doane, Swecker & Mathis, L.L.P.

[57] ABSTRACT

The present invention is related to an integral capillary microcuvette comprising a body member and a cavity including a measuring zone within the body member. The cavity is defined by two opposite, substantially parallel inner surfaces of the body member and includes an outer peripheral edge comprising a sample inlet and an inner peripheral zone having a channel of higher capillary force than the measuring zone. The channel extends around the entire inner peripheral zone with ends of the channel communicating with the atmosphere at the exterior of the microcuvette.

7 Claims, 2 Drawing Sheets

5,674,457

CAPILLARY MICROCUVETTE

BACKGROUND OF THE INVENTION

The present invention concerns a capillary microcuvette. More specifically the invention concerns a disposable integral capillary microcuvette having improved flow for essentially simultaneously sampling a fluid and analyzing of the sample.

A cuvette for sampling a fluid, mixing the sample with a reagent and directly making optical analysis of the sample mixed with the reagent is previously known from U.S. Pat. No. 4,088,448. This cuvette comprises a body member including two planar surfaces defining an optical path and placed at a predetermined distance from one another to determine the optical path length and to define a cavity which includes a measuring zone therein, having an inlet for communicating said cavity with the exterior of the body member- The cavity has a predetermined fixed volume, and the predetermined distance permits the sample to enter the cavity by capillary force. Furthermore, a reagent is coated on the cavity surface, which mixes with the sample and allows the sample to be measured by optical analysis.

This known cuvette has several advantages when compared with the conventionally used devices. It permits sampling of a liquid, mixing and chemically reacting it with a suitable reagent; e.g. for colour development, in the same vessel as the one used for the subsequent measurement. The cuvette disclosed in U.S. Pat. No. 4,088,448 thus simplifies the sampling procedure, reduces the number of devices needed and in most cases, depending on the type of analysis, considerably improves the accuracy of the analysis by making the analyzing procedure independent of the operation of the device.

However, it has been discovered that the microcuvette described in U.S. Pat. No. 4,088,448 may develop air bubbles that can interfere with the optical analysis. Air bubbles generally form in the cavity of the cuvettes because of unsatisfactory sample flow in the cuvette cavity. This is especially detrimental for hemoglobin measurements because of the strong absorption of the hemoglobin. In particular, in a photometric determination, the presence of a large air bubble in the light path traversing the measuring zone will result in an overall measured hemoglobin value below the actual level because the photometer will read the bubble as a contribution of extremely low hemoglobin. Quality control is routinely carried out to discard those cuvettes which include air bubbles, thereby eliminating the risk that air bubbles will be present in the measuring zone when the cuvettes are used in a clinical procedure. A considerable number of cuvettes do not pass the quality control and have to be discarded, thereby increasing the overall cost of the cuvettes.

OBJECT OF THE INVENTION

One object of the present invention is to provide an improved cuvette which eliminates the risk of failure caused by the presence of air bubbles in the measuring zone.

SUMMARY OF THE INVENTION

The above objects and others are accomplished by providing a disposable, integral capillary microcuvette for essentially simultaneous sampling a fluid and analyzing the sample. In connection with the present invention the term "integral" means that the cuvette is made or manufactured in one, integral, piece. The microcuvette comprises a body member and a cavity including a measuring zone within the body member. The cavity is defined by two opposite, substantially parallel inner surfaces of the body member and includes an outer peripheral edge comprising a sample inlet and an inner peripheral zone having a channel of higher capillary force than the measuring zone. The channel extends around the entire inner peripheral zone with ends of the channel communicating with the exterior of the microcuvette.

DETAILED DESCRIPTION OF THE INVENTION

Figure 1:
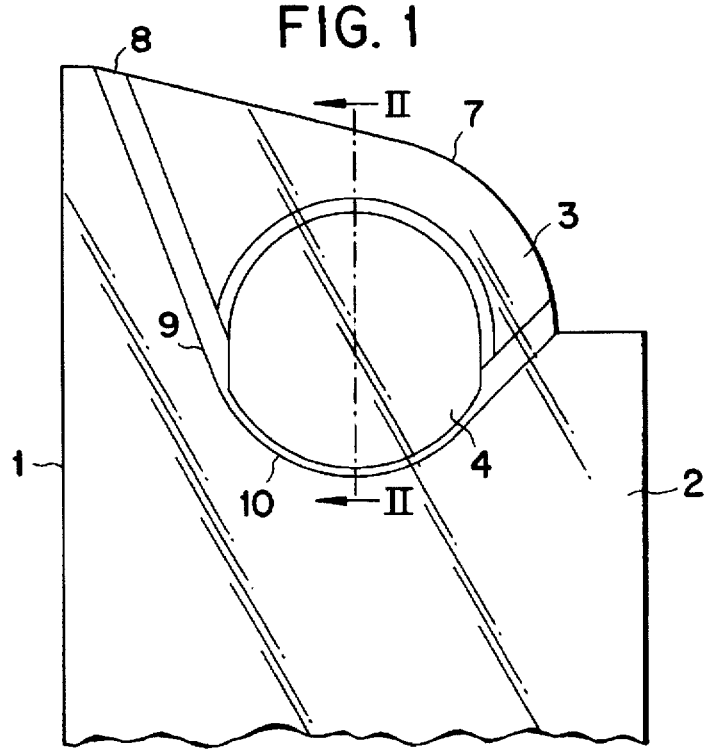
FIG. 1 is a plan view of the microcuvette according to one embodiment of the present invention.
Figure 2:
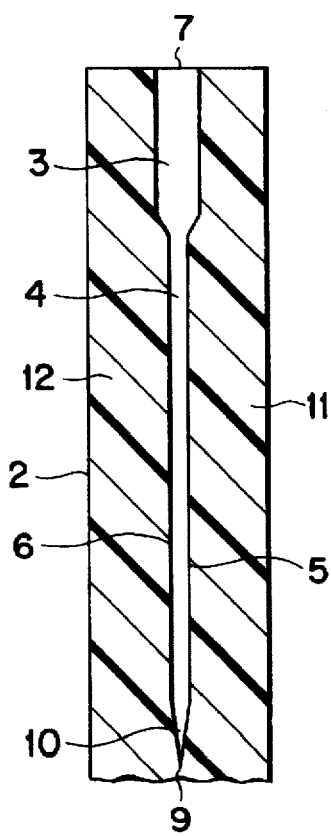
FIG. 2 is a cross sectional view of a microcuvette according to the present invention, taken along line II—II of FIG. 1.

FIG. 1 is a plan view of a microcuvette generally designated by reference numeral 1, according to one embodiment of the present invention. The microcuvette 1, comprises a body member 2, comprised of two substantially planar sheets of material 11, 12, and includes a cavity 3, defined by two inner surfaces 5, 6, of the body member 2. A measuring zone 4 is arranged within the cavity 3. The distance between the surfaces 5, 6, defining the measuring zone 4, is a critical parameter in providing the proper optical path length for the desired measurement. In a preferred embodiment of measuring hemoglobin, the distance should be between 0.05 and 0.15 mm. The distance between the inner surfaces of the rest of the cavity 3 is preferably in the order of 0.3–2 mm, i.e. clearly longer than the distance between the inner surfaces 5, 6 of the measuring zone. An outer peripheral edge 7, includes a sample inlet 8, comprised of the opening between the two sheets 11, 12, making up the body member 2. An inner peripheral zone 9, includes a channel 10, which has a higher capillary force than the measuring zone 4. The channel 10, which can have any shape, extends along the entire inner peripheral zone 9, and communicates with the atmosphere at both ends of the channel 10. The channel 10, preferably has a width between 10 micron and 2 mm.

When a sample liquid is drawn into the cuvette through the inlet 8, the channel 10 is filled along its entire length due to its high capillary action. After filling of the channel the sample liquid propagates into the rest of the cavity 3 in a flow pattern which prevents air bubbles to be captured in the measuring zone 4.

Figure 3:
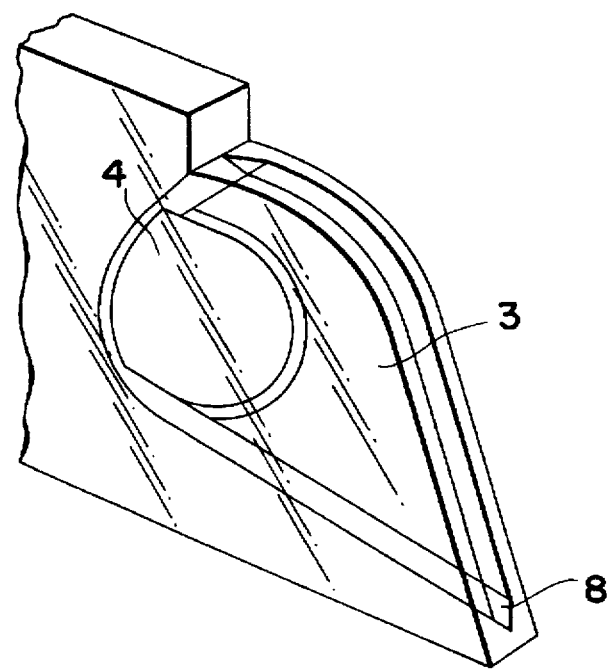
FIG. 3 is a perspective view of the microcuvette according to the invention.
Figure 4:
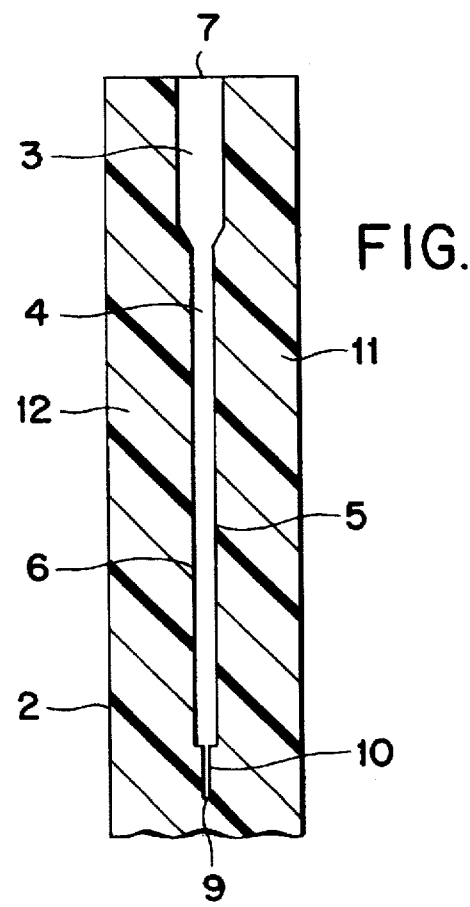
FIG. 4 is a cross-sectional view of a microcuvette according to another embodiment of the present invention.

The provision of the channel having a higher capillary force than the measuring zone thus improves hydrodynamic flow within the cuvette cavity and prevents air bubbles to be trapped in the measuring zone. The channel may have any appropriate shape or form as long as the capillary force of the channel is higher than the capillary force of the measuring zone. This is accomplished by providing a channel having a depth which is less than that of the measuring zone. In particular, the channel may be defined by an inner wall of the inner peripheral zone and by the two opposite, substantially planar, surfaces of the body member whereby the distance between the planar surfaces of the channel is shorter than the distance between the inner surfaces of the measuring zone as shown in FIG. 3.

In an alternative embodiment of the present invention, the distance between the two opposite substantially planar surfaces of the body member continuously increases in a direction extending away from the inner end wall of the inner peripheral zone. In this case the channel is shaped as a wedge, the bottom of which opens towards the measuring zone.

The cuvettes according to the present invention may be formed from any suitable material which allows the formation of the channel and measuring zone to the necessary tight tolerance levels. Preferably, the cuvettes according to the present invention are made of glass or a polymeric material.

Cuvettes according to the present invention were compared with cuvettes according to U.S. Pat. No. 4,088,448 as follows:

A reagent of 40 g sodium desoxycholate 18 g sodium azid and 20 g sodium nitrite per liter solvent was prepared.

100 cuvettes according to U.S. Pat. No. 4,088,448 available from HemoCue AB, Sweden, and 100 cuvettes according to the present invention were filled with the above reagent, air dried and examined optically for uniform drying pattern. The cuvettes were then filled with whole blood, EDTA and an anticoagulating agent. A hemoglobin measurement was then carried out according to a modified azidmethemoglobin method according to Vanzetti described in J. Lab. Clin. Med. 67, 116–26 (1966) wherein the measurement is made at 570 and 880 nm respectively. The number of cuvettes which exhibited air bubbles was recorded.

| Type of Cuvette | Number with air bubble |
| --- | --- |
| U.S. Pat. No. 4,088,448 | 25 |
| The invention | 0 |

As is apparent from the above, the cuvettes according to the present invention are very advantageous in eliminating the risks associated with the occurrence of air bubbles within the measuring zone. By providing the cuvette according to the present invention with a channel having higher capillary force than that of the measuring zone, air bubbles were entirely eliminated. This not only reduced the costs associated with discarded cuvettes but also greatly reduces the risk of improper readings which occur because of air bubbles.

The present invention has been described above with respect to the measurement of hemoglobin. However, the present invention is equally applicable to the measurement of other blood chemistry values, such as glucose, blood urea nitrogen, albumin, bilirubin, and total protein, etc. Furthermore, the present invention is applicable to numerous other analytical measurements and tests outside the blood chemistry field.

The foregoing has been a description of certain preferred embodiments of the present invention, but it is not intended to limit the invention in any way. Rather, many modifications, variations, and changes in details may be made within the scope of the present invention.

What is claimed is:

1. An integral capillary microcuvette comprising a body member having an outer peripheral edge, the body member being provided with a cavity that communicates with the outer peripheral edge of the body member, the cavity being defined by two opposing inner surfaces of the body member, a portion of the cavity defining a measuring zone within the body member, the cavity having an inner peripheral zone at which is located a channel, the channel extending along the entire inner peripheral zone of the cavity, the channel being sized relative to the measuring zone such that the channel has a higher capillary force than the measuring zone to prevent air bubbles from becoming trapped in the measuring zone, the outer peripheral edge of the body member being provided with a sample inlet through which a sample is drawn into the body member, the sample inlet being in communication with the channel and the channel being in communication with the measuring zone.

2. A microcuvette according to claim 1, wherein said cavity has a predetermined volume.

3. A microcuvette according to claim 1, wherein said cavity includes a dry reagent in a predetermined amount.

4. A microcuvette according to claim 1, wherein the distance between the inner surfaces of the body member at said measuring zone does not exceed 0.15 mm.

5. A microcuvette according to claim 1, wherein said channel is defined by an inner end wall at said inner peripheral zone and two substantially planar portions of the inner surfaces of said body member.

6. A microcuvette according to claim 5, wherein said two substantially planar portions are parallel and the distance between the two substantially planar portions is less than the distance between portions of the inner surfaces of the body member at said measuring zone.

7. A microcuvette according to claim 5, wherein the distance between the two substantially planar surfaces of said body member increases in a direction extending away from said inner end wall of said inner peripheral zone.

\* \* \* \* \*

(12) EX PARTE REEXAMINATION CERTIFICATE (6005th)

United States Patent
Williamsson et al.

(10) Number: US 5,674,457 C1
(45) Certificate Issued: Nov. 13, 2007

(54) CAPILLARY MICROCUVETTE

(75) Inventors: Anders Williamsson, Helsingborg (SE); Stefan Wahlqvist, Lomma (SE); Sven-Erik Nilsson, Helsingborg (SE); Jan Lilja, Helsingborg (SE); Lars Jansson, Ängelholm (SE); Bertil Nilsson, Bjärred (SE)

(73) Assignee: Hemocue AB, Angelholm (SE)

Reexamination Request:
No. 90/007,584, Jun. 13, 2005

Reexamination Certificate for:
Patent No.: 5,674,457
Issued: Oct. 7, 1997
Appl. No.: 08/429,494
Filed: Apr. 26, 1995

(51) Int. Cl.
*G01N 21/03* (2006.01)

(52) U.S. Cl. .................. 422/102; 356/246; 422/99; 422/104

(58) Field of Classification Search .................. None
See application file for complete search history.

(56) References Cited

U.S. PATENT DOCUMENTS

| | | |
|---|---|---|
| 2,015,949 A | 10/1935 | Maw |
| 2,056,791 A | 10/1936 | Logan |
| 2,059,374 A | 11/1936 | Logan et al. |
| 2,062,587 A | 12/1936 | Logan et al. |
| 2,062,588 A | 12/1936 | Logan et al. |
| 2,069,374 A | 2/1937 | Lagomarsino |
| 3,363,503 A | 1/1968 | Shifrin |
| 3,501,242 A | 3/1970 | DeMey, II et al. |
| 3,565,537 A | 2/1971 | Fielding |
| 3,698,822 A | 10/1972 | Polanyi |
| 3,705,000 A | 12/1972 | Guerra |
| 3,814,522 A | 6/1974 | Clark et al. |
| 3,905,702 A | 9/1975 | Johnson |
| 3,961,346 A | 6/1976 | White |
| 4,088,448 A | 5/1978 | Lilja et al. |
| 4,088,488 A | 5/1978 | Chang et al. |
| 4,405,235 A | 9/1983 | Rossiter |
| 4,596,695 A | 6/1986 | Cottingham |
| 4,654,197 A | 3/1987 | Lilja et al. |
| 4,746,215 A | 5/1988 | Gross |
| 4,756,884 A | 7/1988 | Hillman et al. |
| 4,761,381 A | 8/1988 | Blatt et al. |
| 4,865,812 A | 9/1989 | Kuntz et al. |
| 4,957,582 A | 9/1990 | Columbus |
| 4,981,654 A | 1/1991 | Kuntz |
| 5,030,421 A | 7/1991 | Muller |
| 5,147,607 A | 9/1992 | Mochida |
| D337,388 S | 7/1993 | Nilsson et al. |
| 5,260,032 A | 11/1993 | Muller |
| 5,286,454 A | 2/1994 | Nilsson et al. |
| 5,674,457 A | 10/1997 | Williamsson et al. |

FOREIGN PATENT DOCUMENTS

| | | |
|---|---|---|
| EP | 0-287-883 | 10/1988 |
| EP | 0359447 | 3/1990 |
| EP | 0215419 | 5/1991 |
| EP | 821784 B1 * | 11/1998 |
| FR | 2325920 | 9/1976 |
| GB | 2090659 | 12/1981 |
| JP | 2-17426 | 11/1990 |
| WO | 85/04255 | 3/1985 |

OTHER PUBLICATIONS

EKF's Notice of Appeal to the Duesseldorf Higher District Court (against Dusseldorf District Court's judgment of Mar. 9, 2006), dated Mar. 20, 2006 (in English and German).

(Continued)

*Primary Examiner*—Stephen Stein

(57) ABSTRACT

The present invention is related to an integral capillary microcuvette comprising a body member and a cavity including a measuring zone within the body member. The cavity is defined by two opposite, substantially parallel inner surfaces of the body member and includes an outer peripheral edge comprising a sample inlet and an inner peripheral zone having a channel of higher capillary force than the measuring zone. The channel extends around the entire inner peripheral zone with ends of the channel communicating with the atmosphere at the exterior of the microcuvette.

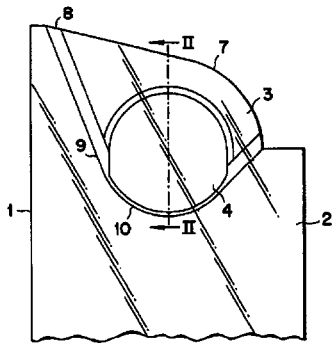

OTHER PUBLICATIONS

EKF's Appeal to the Duesseldorf Higher District Court, dated Jul. 12, 2006 (in English and German).
A German court Judgment promulgated on May 2, 2007 in German nullity action 4 Ni 45/05 (EU)–EP 0 821 784 (DE 696 00 928) (Original in German and English Translation).
A request for accelerated proceedings in German nullity action 4 Ni 45/05(EU)—EP 0 821 784 (DE 696 00 928).
Submission of Feb. 15, 2007 to Higher District Court of Dusseldorf (in English and German).
Group of Tables Comparing The Disclosure of White—3,961,346.
Group of Tables Comparing The Disclosure of Johnson—3,905,702.
Group of Tables Comparing The Disclosure of Lilja et al.—4,088,448.
Group of Tables Comparing The Disclosure of Nilsson et al.—D377,388.
Group of Tables Comparing The Disclosure of Lilja et al.—4,654,197.
Group of Tables Comparing The Disclosure of Nilsson et al.—5,286,454.
Defendant HemoCue's Initial Brief On Patent Claim Construction.
First Office Action of the U.S. Patent No. 5,674,457.
First Office Action Response of the U.S. Patent No. 5,674,457.
Second Office Action of the U.S. Patent No. 5,674,457.
Second Office Action of the U.S. Patent No. 5,674,457; Notice of Allowability; and Information Disclosure Statement.
Assignee's (HemoCue) Claim Construction Chart.
Request for Approval of Proposed New Drawing Figure.
Interview Summary.
Complaint filed in EKF–Diagnostic Sales, *GmbH* v. *HemoCue et al.* (Case No. SA04CA0807).
EKF's brief to the District Court of Duesseldorf dated Feb. 13, 2006 (German pleading and English translation).
HemoCue's reply brief to the District Court of Duesseldorf dated Feb. 16, 2006 (German pleading and English translation).
EKF's response brief to the District Court of Duesseldorf dated Feb. 20, 2006 (German pleading and English translation).
Judgment of the District Court of Duesseldorf, dated Mar. 9, 2006 (German with English translation).
Vanzetti, Guilio, An Azide–Methemoglobin Method for Hemoglobin Determination in Blood, J. Lab. & Clin. Med., Jan. 1966, pp. 116–126, vol. 67.
Factor & Lake, Letter regarding reexamination proceeding, Sep. 19, 2005.
HEMOCUE, engineering drawing dated Jan. 1995, of molding insert used to make cuvettes sold in the U.S. prior to the filing date of the '457 patent.
HEMOCUE, Color copy of operation manual for cuvettes sold prior to '457 patent filing date.
BIOTEST, Opposition filed before the European Patent Office–Opposition Division, Aug. 3, 1999.
HEMOCUE, Reply to Biotest Opposition, Jan. 18, 2000.
EPO, Preliminary Opinion of the Opposition Division and Summons for Oral Proceedings, Jul. 4, 2000.
BIOTEST, Statement to EPO–Opposition Division (in English and German), Oct. 17, 2000.
HEMOCUE, Reply to Biotest Statement filed Oct. 17, 2000, Nov. 6, 2000.
EPO–Opposition Division, Official Minutes from the Oral Proceeding.
EPO–Opposition Division, Decision Revoking European Patent No.: 0821784, Dec. 1, 2000.
HEMOCUE, Notice of Appeal, Jan. 24, 2001.
HEMOCUE, Grounds of Appeal, Mar. 30, 2001.
BIOTEST, Submission to the EPO Appeal Board, Nov. 6, 2001.
HEMOCUE, Reply to Biotest Submission to Board filed Nov. 6, 2001, Mar. 21, 2002.
EPO Appeal Board, Decision Reinstating the Patent.
Nicholaus Preissner, Class Runnberg, Berthold Walter and William Pippen, Declarations filed explaining circumstances surrounding HemoCue's acquisition of Biotest pending appeal.
HemoCue's Trademark Registration No.: 2,268,645 for cuvette design.
Documents relating to HemoCue's 510(k) submission for marketing and approval of the microcuvette, Jun. 1983.
FDA–related documents referenced as #3 and #4 in Factor & Lake letter.
Excerpts from HemoCue's 510(k) submission to the FDA in 1983.
STANBIO, Original Complaint, Oct. 29, 2003.
EKF, Complaint for Declatory Judgment, Sep. 2003.
EKF, First Amended Complaint, May 2, 2005.
STANBIO, Amended Complaint, May 2, 2005.
HEMOCUE, Original Answer to Stanbio's Original Complaint, Jan. 4, 2005.
HEMOCUE, Original Counterclaim, Jan. 4, 2005.
HEMOCUE, Original Answer to EKF's Complaint for Declatory Judgment, Jan. 4, 2005.
EKF, Proposed Claim Constructions, Mar. 29, 2005.
HEMOCUE, Inc., Proposed Claim Constructions, Mar. 29, 2005.
EKF, Markman Brief in Support of its Proposed Claim Construction, May 2, 2005.
HEMOCUE, Defendant's Initial Brief on Claim Construction, May 2, 2005.
HEMOCUE, Statement of Claim (in English and Geramn), Feb. 3, 2005.
EKF, Response (in English and German), Sep. 6, 2005.
EKF, Nullity Proceeding against German counterpart to HemoCue's '457 patent (in English and German), Sep. 2, 2005.

\* cited by examiner

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–7 is confirmed.

* * * * *